United States Patent [19]

Carle

[11] Patent Number: 4,605,549

[45] Date of Patent: Aug. 12, 1986

[54] SYNERGISTIC PESTICIDAL COMPOSITIONS OF (S)α-CYANO-3-PHENOXY-BENZYL (1R,CIS) 2,2-DIMETHYL-3-(2,2-DIBROMOVINYL)-CYCLOPROPANE-1-CARBOXYLATE AND (R,S) ALLETHRONYL D-TRANS CHRYSANTHEMATE

[75] Inventor: Pierre R. Carle, Rognonas, France

[73] Assignee: Roussel Uclaf, Paris, France

[21] Appl. No.: 633,146

[22] Filed: Jul. 23, 1984

Related U.S. Application Data

[63] Continuation of Ser. No. 347,279, Feb. 9, 1982, abandoned.

[30] Foreign Application Priority Data

Feb. 20, 1981 [FR] France .................. 81 03403

[51] Int. Cl.$^4$ .................. A61L 9/04; A01N 25/00; A01N 37/34; A01N 53/00
[52] U.S. Cl. .................. 424/18; 424/45; 514/521; 514/531
[58] Field of Search .................. 424/304, 45, 18; 514/521, 531

[56] References Cited

U.S. PATENT DOCUMENTS

| | | | |
|---|---|---|---|
| 2,768,965 | 10/1956 | Stansbury et al. | 560/124 |
| 3,714,153 | 1/1973 | Martel et al. | 424/275 |
| 3,819,823 | 6/1974 | Okuno | 424/306 |
| 3,899,586 | 8/1975 | Okuno et al. | 424/274 |
| 3,973,036 | 8/1976 | Hirano et al. | 424/304 |
| 4,024,163 | 5/1977 | Elliott et al. | 424/304 |

*Primary Examiner*—Allen J. Robinson
*Attorney, Agent, or Firm*—Bierman, Peroff & Muserlian

[57] ABSTRACT

Novel synergistic pesticidal compositions comprising of a mixture of at least one stereoisomer of α-cyano-3-phenoxy-benzyl (1R,cis) 2,2-dimethyl-3-(2,2-dihalovinyl)-cyclopropane-1-carboxylate wherein the halogen is chlorine or bromine and at least one compound selected from the group consisting of all stereoisomer forms of allethronyl chrysanthemates and all possible stereoisomer forms of 5-benzyl-3-furyl-methyl 2,2-dimethyl-3-(2-oxo-2,3,4,5-tetrahydro-3-thiophenylidenemethyl)-cyclopropane-1(R)-carboxylate and a method of killing insects.

8 Claims, No Drawings

SYNERGISTIC PESTICIDAL COMPOSITIONS OF (S)α-CYANO-3-PHENOXY-BENZYL (1R,CIS) 2,2-DIMETHYL-3-(2,2-DIBROMOVINYL)-CYCLO-PROPANE-1-CARBOXYLATE AND (R,S) ALLETHRONYL D-TRANS CHRYSANTHEMATE

PRIOR APPLICATION

This application is a continuation of copending U.S. patent application Ser. No. 347,279 filed Feb. 9, 1982, now abandoned.

STATE OF THE ART

Synergistic insecticidal compositions are known containing (S)α-cyano-3-phenoxy-benzyl (1R,cis) 2,2-dimethyl-3-(2,2-dibromovinyl)-cyclopropane-1-carboxylate [compound X] or (S)α-cyano-3-phenoxy-benzyl (1R,cis) 2,2-dimethyl-3-(2,2-dichlorovinyl)-cyclopropane-1-carboxylate [compound X'] and different pyrethrinoid compounds.

OBJECTS OF THE INVENTION

It is an object of the invention to provide novel synergistic pesticidal compositions.

It is another object of the invention to provide a novel method of killing pests, especially insects.

These and other objects and advantages of the invention will become obvious from the following detailed description.

THE INVENTION

The novel synergistic compositions of the invention are comprised of a pesticidally effective amount of a mixture of at least one stereoisomer of α-cyano-3-phenoxy-benzyl (1R,cis) 2,2-dimethyl-3-(2,2-dihalovinyl)-cyclopropane-1-carboxylate wherein the halogen is chlorine or bromine and at least one compound selected from the group consisting of all stereoisomer forms of allethronyl chrysanthemates and all possible stereoisomer forms of 5-benzyl-3-furyl-methyl 2,2-dimethyl-3-(2-oxo-2,3,4,5-tetrahydro-3-thiophenylidenemethyl)-cyclopropane-1-carboxylate.

The preferred compositions of the invention are comprised of a pesticidally effective amount of a mixture of (A) (S)α-cyano-3-phenoxy-benzyl (1R,cis) 2,2-dimethyl-3-(2,2-dibromovinyl)-cyclopropane-1-carboxylate or (S)α-cyano-3-phenoxy-benzyl (1R,cis) 2,2-dimethyl-3-(2,2-dichlorovinyl)-cyclopropane-1-carboxylate and (B) at least one member of the group consisting of (RS) allethronyl dl (cis trans) chrysanthemate, (RS) allethronyl d (cis trans) chrysanthemate, (RS) allethronyl d trans chrysanthemate, (S) allethronyl d trans chrysanthemate, (R) allethronyl d trans chrysanthemate and 5-bensyl-3-furylmethyl 2,2-dimethyl-3-[(S)(2-oxo-2,3,4,5-tetrahydro-3-thiophenylidene)-methyl]-cyclopropane-1R-carboxylate.

The compositions of the invention must contain one of the (A) components and can contain at least one of the (B) components in variable proportions and possibly other active ingredients. If component (B) is (RS) allethronyl d (cis trans) chrysanthemate, the mixture preferably contains 80% by weight of the trans isomer and 20% of the cis isomer. If the (B) component is a mixture of (S) allethronyl d-trans chrysanthemate and (R) allethronyl d-trans chrysanthemate, the mixture preferably contains 75% by weight of the (S) allethronyl ester and 25% weight of the (R) allethronyl ester.

More preferred compositions of the invention are comprised of a mixture of (S)α-cyano-3-phenoxy-benzyl (1R,cis) 2,2-dimethyl-3-(2,2-dibromovinyl)-cyclopropane-1-carboxylate and either (R,S) allethronyl d-trans chrysanthemate or (R,S) allethronyl d (cis trans) chrysanthemate or 5-benzyl-3-furylmethyl 2,2-dimethyl-3-[(S)(2-oxo-2,3,4,5-tetrahydro-3-thiophenylidene)-methyl]-cyclopropane-1(R)-carboxylate.

The most preferred compositions of the invention are (a) mixtures of 50%±20% by weight of (S)α-cyano-3-phenoxy-benzyl (1R,cis) 2,2-dimethyl-3-(2,2-dibromovinyl)-cyclopropane-1-carboxylate and 50%±20% by weight of (R,S) allethronyl d-trans chrysanthemate, (b) mixtures of 75%±10% by weight of (S)α-cyano-3-phenoxy-benzyl (1R,cis) 2,2-dimethyl-3-(2,2-dibromovinyl)-cyclopropane-1-carboxylate and 25%±10% by weight of 5-benzy-3-furyl-methyl 2,2-dimethyl-3-[(S)(2-oxo-2,3,4,5-tetrahydro-3-thiophenylidene)-methyl]-cyclopropane-1(R)-carboxylate and (c) mixtures of 25%±10% by weight of (S)α-cyano-3-phenoxy-benzyl (1R,cis) 2,2-dimethyl-3-(2,2-dibromovinyl)-cyclopropane-1-carboxylate and 75%±10% by weight of (R,S) allethronyl d (cis trans) chrysanthemate.

The compositions may also contain the adjuvants necessary for aerosol sprays or for use in the form of fumigant compositions. In the latter compositions advantageously have for their inactive portion a combustible serpentine or coil base or an incombustible fibrous substrate. In the latter case, the fumigant obtained after incorporation of the active ingedient of formula I is placed in a heating apparatus such as an electromosquitoe destroyer.

The compositions may also be prepared as a spraying oil containing the active ingredient and the oil may soak the wick of a lamp wich is then subjected to combustion.

The compositions of the invention may also contain one or more other active ingredients and besides being in the form of aerosol sprays or fumigants, the compositions may be in the form of powders, granules, suspensions, emulsions, solutions, baits and other preparations classically used for compounds of this type.

Besides the active ingredient, the compositions generally contain a vehicle and/or a nonionic surface active agent to ensure a uniform dispersion of the substances in the mixture. The vehicle used may be a liquid such as water, alcohol, hydrocarbons or other organic solvents or a mineral, animal or vegetable oil or a powder such as talc, clays, silicates or Kieselguhr or a combustible solid such as tabu powder or pyrethrum residue.

To increase the pesticidal activity of the compositions of the invention, classical pyrethrinoid synergists may be incorporated therein such as 1-(2,5,8-trioxadodecyl)-2-propyl-4,5-methylenedioxy-benzene (piperonyl butoxide) or N-(2-ethylheptyl)-bicyclo-[2,2-1]5-heptene-2,3-dicarboxyimide or piperonyl-bis-2-(2'-n-butoxy-ethoxy)-ethyl acetal (tropital).

The pesticidal compositions of the invention are more particularly intented for combatting insects.

The insecticidal compositions of the invention preferably contain 0.005 to 10% by weight of the mixture of active ingredients. Besides the insecticidal field, the compositions may be used, for example, as acaricides to combat vegetable parasites or warm-blooded animal parasites. Generally, the compositions may be used in the agricultural field and in the home. The test data in the examples shows the synergistic insecticidal activity of the compositions against houseflies and the synergistic activity permits an economy due to the use of lower doses of the active compounds to obtain an effective activity.

The novel method of the invention for combatting parasites such as acariens or insects comprises contacting the parasites with a pesticidally effective amount of the synergistic mixture of the invention.

In the following examples there are described several preferred embodiments to illustrate the invention. However, it should be understood that the invention is not intended to be limited to specific embodiments.

EXAMPLE 1

An emulsifiable concentrate was prepared by intimately mixing 0.015 g of a 1-1 mixture of (S)α-cyano-3-phenoxy-benzyl (1R,cis) 2,2-dimethyl-3-(2,2-dibromovinyl)-cyclopropane-1-carboxylate [compound X] and (R,S) allethronyl d-trans chrysantemate [compound Y], 0.5 g of piperonyl butoxide, 3.5 g of Tween 80, 0.1 g of Topanol A and 95.885 g of xylene.

EXAMPLE 2

A soluble concentrate or aqueous spray was prepared by intimately mixing 0.25 g of a 3-1 mixture of compound X and 5-benzyl-3-furyl-methyl 2,2-dimethyl-3-[(S)(2-oxo-2,3,4,5-tetrahydro-3-thiophenylidene)-methyl]-cyclopropane-1-carboxylate [compound Z], 1 g of piperonyl butoxide, 0.25 g of Tween 80, 0.1 g of Topanol A and 98.4 g of water.

EXAMPLE 3

A fumigant composition was prepared by homogenously mixing 0.25 g of a 1-3 mixture of compound X and (R,S) allethronyl d(cis trans) chrysanthemate [compound T], 25 g of tabu powder, 40 g of cedar needle powder, 33.75 g of pine-wood powder, 0.5 g of brilliant green and 0.5 g of p-nitrophenol.

SYNERGISTIC INSECTICIDAL ACTIVITY 50 female Musca houseflies aged 4 to 5 days were introduced for each test into a glass Kearns and March cylinder and 500 mg of the insecticidal solution was sprayed therein after the flies were freed. The number of insects knocked down were counted every 30 seconds for 15 minutes. 5 minutes after the last counting, the cylinder was aired and the flies were gathered and placed in a one liter wide mouth bottle provided with damp cotton to ensure the survival of he insects which recovered after the test in a storage room. The number of living and dead insects was determined after 24 hours.

For each association of products, the two components were used alone in the test at a concentration of 500 mg/l as well as mixtures thereof at the same concentration and in the proportion defined in the data study. Each test of the test compound or mixture was run 10 times with the spraying being effected with nitrogen as propellant and Isopar L as solvent at a pressure of 1 bar for one second. The treatment room was at a temperature of 23°±2° C. and a relative humidity of 84%±8% and the storage room was at a temperature of 21°±1° C. and a relative humidity of 83%±10%.

The results were expressed by the method of Sun et al [Journ. Econ. Entom., Vol. 53, No. 5, p. 887–892] to determine the $KT_{50}$ of each produce alone (time necessary to cause a 50% knockdown of the test insects) and the $KT_{50}$ for each mixture of the products in the following proportions: 0.001+0.999; 0.010+0.990; 0.100+0.900; 0.250+0.750; 0.500+0.500; 0.750+0.250; 0.900+0.100; 0.990+0.010; and 0.999+0.001, in the solution at identical concentrations.

The co-toxicity index was calculated by the following method : A and B are the two constituents of mixture M, $KT_{50}A$ and $KT_{50}B$ are the $KT_{50}$ of each of them with $KT_{50}B > KR_{50}A$, $KT_{50}(A+B)$ is the $KT_{50}$ of the mixture. The true toxicity index of the A+B mixture with respect to A is $[KT_{50}A/KT_{50}(A+B)] \times 100$ and the real toxicity index of B with respect to A is $KT_{50}A/KT_{50}B \times 100$. The real toxicity index of A with respect to A is $KT_{50}A/KT_{50}A \times 100$.

The theoretical toxicity index of the mixture is determined as [real toxicity index of A x % of A in the mixture]+[real toxicity index of B x % of B in the mixture]. or $$\left( \frac{KT_{50}A}{KT_{50}A} \times 100 \right) \text{ (\% A in mixture } M) +$$

$$\left( \frac{KT_{50}A}{KT_{50}A} \times 100 \right) \text{ (\% B in mixture } M)$$

or $$100 \times \text{\% of } A \text{ in mixture } M +$$

$$\left( \frac{KT_{50}A}{KT_{50}B} \times 100 \right) \text{ (\% B in mixture } M)$$

The co-toxicity index of the mixture is calculated as real index of mixture/theoretical index of mixture × 100.

When the co-toxicity index of the mixture is equal to 100, it means that there is only an additive effect, greater than 100 indicates synergism and less than 100% indicates antagonism. The synergism or antagonism greater than 30% as compared to 100 (<70 or >130) are the only values considered. The results are reported in the following tables.

TABLE I

| PRODUCTS | Average Weight of 100 flies | Average Weight in mg of spray | Average $KT_{50}$ (in mn) | Average % of mortality at 24 h |
|---|---|---|---|---|
| 0.5 g/l of compound X | 2,04 ± 0,12 | 518,8 ± 4,7 | 4,48 ± 0,16 | 100 |
| 0.5 g/l of compound Y | 2,01 ± 0,09 | 518,6 ± 4,4 | 3,27 ± 0,18 | 37,4 ± 7,6 |
| 50/50 mixture of Compounds X + Y 0.5 g/l | 2,05 ± 0,11 | 517,8 ± 4,1 | 2,90 ± 0,26 | 100 |

The real toxicity index of the mixture is 154.5; the theoretical toxicity index of the mixture is 118.5 and the co-toxicity index of the mixture is 130.4 which means that the 1-1 mixture of compounds X and Y shows a synergistic effect.

TABLE II

| PRODUCTS | Average Weight of 100 flies | Average Weight in mg of spray | Average $KT_{50}$ in min. | Average % of mortality at 24 h |
|---|---|---|---|---|
| 0.5 g/l of compound X | 1,95 ± 0,08 | 515,7 ± 3,5 | 4,19 ± 0,13 | 100 |

TABLE II-continued

| PRODUCTS | Average Weight of 100 flies | Average Weight in mg of spray | Average $KT_{50}$ in min. | Average % of mortality at 24 h |
|---|---|---|---|---|
| 0.5 g/l of compound Z | 1,94 ± 0,08 | 511,3 ± 11,4 | 1,83 ± 0,20 | 9,04 ± 4,1 |
| 3-1 mixture of compounds X + Z 0.5 g/l | 1,93 ± 0,08 | 515,2 ± 3,8 | 2,11 ± 0,12 | 100 |

The real toxicity index of the mixture was 198.6; the theoretical toxicity of the mixture was 132.2 and the cotoxicity index of the mixture was 150.2 which means that the 3-1 mixture of compounds X+Z showed a net synergistic effect in the knock down ability of the products.

TABLE III

| PRODUCTS | Average Weight of 100 flies | Average Weight in mg of spray | Average $KT_{50}$ in min | Average % of Mortality at 24 h |
|---|---|---|---|---|
| 0.5 g/l compound X | 2,03 ± 0,15 | 521 ± 3,80 | 3,90 ± 0,20 | 100 |
| 0.5 g/l of compound T | 2,03 ± 0,15 | 521 ± 3,13 | 3,37 ± 0,22 | 98,6 ± 2,31 |
| 0.5 g/l of 1-3 mixture of compounds X + T | 2,03 ± 0,15 | 522 ± 3,43 | 2,61 ± 0,23 | 100 |

The real toxicity index of the mixture is 149.42, the theoretical toxicity index of the mixture is 111.80 and the co-toxicity index of the mixture is 133.65 which means that the 1-3 mixture of compounds X and T shows a synergistic effect on the knock down ability of the products.

Various modifications of the compositions and method of the invention may be made without departing from the spirit or scope thereof and it is to be understood that the invention is to be limited only as defined in the appended claims.

What I claim is:

1. An insecticidal composition consisting essentially of a synergistically effective amount of about 1:1 ratio by weight of (S) α-cyano-3-phenoxy-benzyl (1R,cis) 2,2-dimethyl-3-(2,2-dibromovinyl)-cyclopropane-1-carboxylate and (R,S) allethronyl d-trans chrysanthemate.

2. A composition of claim 1 also containing adjuvants for aerosol sprays.

3. A composition of claim 1 also containing adjuvants for fumigant compositions.

4. A composition of claim 2 in the form of a fumigant coil or serpentine.

5. A composition of claim 3 wherein the active mixture is incorporated into combustible oil.

6. A method of combatting insects comprising contacting the insects with an insecticidally effective amount of a mixture of claim 1.

7. A method of claim 6 wherein the mixture also contains adjuvants for aerosol sprays.

8. A method of claim 6 wherein the mixture also contains adjuvants for fumigants.

* * * * *